(12) United States Patent
Ebenbeck et al.

(10) Patent No.: US 7,238,722 B2
(45) Date of Patent: Jul. 3, 2007

(54) PYRAZOLYLALKINES

(75) Inventors: Wolfgang Ebenbeck, Leverkusen (DE); Florian Rampf, Köln (DE); Albrecht Marhold, Leverkusen (DE)

(73) Assignee: LANXESS Deutschland GmbH, Leverkusen (DE)

( * ) Notice: Subject to any disclaimer, the term of this patent is extended or adjusted under 35 U.S.C. 154(b) by 362 days.

(21) Appl. No.: 10/751,761

(22) Filed: Jan. 5, 2004

(65) Prior Publication Data

US 2004/0229929 A1    Nov. 18, 2004

(30) Foreign Application Priority Data

Jan. 7, 2003    (DE) ................ 103 00 122

(51) Int. Cl.
*A61K 31/415* (2006.01)
*C07D 231/06* (2006.01)
*C07D 45/02* (2006.01)

(52) U.S. Cl. ................. 514/406; 548/356.1; 548/364.1
(58) Field of Classification Search ................ 514/406; 548/356.1, 364.1
See application file for complete search history.

(56) References Cited

U.S. PATENT DOCUMENTS

| 3,240,796 | A | 3/1966 | Thoma et al. | 260/453 |
| 3,326,958 | A | 6/1967 | Curtius et al. | 260/463 |
| 5,300,521 | A | 4/1994 | Eberle et al. | 514/406 |
| 2002/0156115 | A1 | 10/2002 | Oda et al. | 514/407 |
| 2003/0191171 | A1 | 10/2003 | Oda et al. | 514/406 |

FOREIGN PATENT DOCUMENTS

FR    1.483.560    6/1967

*Primary Examiner*—Kamal A. Saeed
(74) *Attorney, Agent, or Firm*—Michael A. Miller

(57) ABSTRACT

The present invention relates to pyrazolyalkines and to their use, to a process for preparing them and also to intermediates.

18 Claims, No Drawings

PYRAZOLYLALKINES

BACKGROUND OF THE INVENTION

1. Field of the Invention

The present invention relates to pyrazolylalkines and to processes for preparing and using them and also to their intermediates.

2. Brief Description of the Prior Art

Pyrazolylalkines have gained industrial significance, in particular, as intermediates for the preparation of insecticides and acaricides (see also EP-A 571 326 and EP-A 1 219 173). Illustrative thereof is 4-pyrazolylphenylalkines which can be prepared, for example, by palladium-catalysed coupling of phenylalkines with iodopyrazoles. This process is however, disadvantaged in that some phenylalkines, for example 3,5-bis(trifluoromethyl)phenylalkine, tend to be susceptible spontaneous and uncontrolled decomposition. In addition, iodopyrazoles can only be obtained in moderate yields by iodinating the corresponding pyrazoles.

There is therefore a need for a process which, starting from easily obtainable reactants, enables the reliable preparation of pyrazolylalkines.

SUMMARY OF THE INVENTION

A process has now been found for preparing compounds of the formula (I)

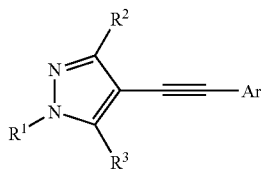

(I)

in which $R^1$ is hydrogen, $C_1$-$C_{12}$-alkyl, $C_5$-$C_{14}$-aryl, $C_6$-$C_{15}$-arylalkyl, $C_1$-$C_{12}$-fluoroalkyl or radicals of the formula (II)

($C_1$-$C_8$-alkylene)-B-D-E  (II)

and $R^2$ und $R^3$ are each independently hydrogen, $C_1$-$C_{12}$-alkyl, $C_1$-$C_{12}$-alkoxy, $C_5$-$C_{14}$-arkyl, $C_5$-$C_{14}$-aryloxy, $C_6$-$C_{15}$-arylalkyl, $C_6$-$C_{15}$-arylalkoxy, chlorine, fluorine, cyano, free or protected -formyl, $C_1$-$C_{12}$-fluoroalkyl, $C_1$-$C_{12}$-fluoroalkylthio, $C_1$-$C_{12}$-fluoroalkoxy or radicals of the formulae (IIIa) to (IIIf), A-B-D-E  (IIIa)

A-E  (IIIb)

A-SO$_2$-E  (IIIc)

A-B-SO$_2$R$^5$  (IIId)

A-SO$_3$W  (IIIe)

A-COW  (IIIf)

where, in the formulae (II) and (IIIa) to (IIIf),

A is absent or is a $C_1$-$C_8$-alkylene, $C_1$-$C_8$-alkenylene or $C_1$-$C_8$-fluoroalkylene radical and B is absent or is oxygen, sulphur or NR$^4$ where
  $R^4$ is hydrogen, $C_1$-$C_8$-alkyl, $C_6$-$C_{15}$-arylalkyl or $C_5$-$C_{14}$-aryl and D is a carbonyl group and E is $R^5$, OR$^5$, NHR$^6$ or N(R$^6$)$_2$,
  where
  $R^5$ is $C_1$-$C_8$-alkyl, $C_6$-$C_{15}$-arylalkyl or $C_5$-$C_{14}$-aryl and
  $R^6$ is in each case independently $C_1$-$C_8$-alkyl, $C_6$-$C_{15}$-arylalkyl or $C_6$-$C_{14}$-aryl, or N(R$^6$)$_2$ together is a cyclic amino radical having 4 to 12 carbon atoms and
  W is OH, NH$_2$ or OM where M is an alkali metal ion, half an equivalent of an alkaline earth metal ion, an ammonium ion or an organic ammonium ion and Ar is a mono-, bi- or tricyclic aromatic radical having a total of 5 to 18 ring atoms, and in which at most one ring atom per cycle is selected from the group of oxygen, sulphur and nitrogen, and the mono-, bi- or tricyclic aromatic radical is optionally mono- or polysubstituted, which is characterized in that in one step, a), the compounds of the formula (IV)

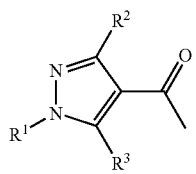

(IV)

in which $R^1$, $R^2$ and $R^3$ are each independently as defined above are initially converted by halogenation and elimination to compounds of the formula (V)

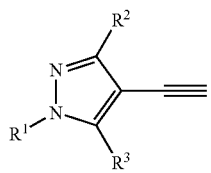

(V)

and in one step, b), the compounds of the formula (V) are converted to compounds of the formula (I) by reacting with compounds of the formula (V)

Hal-Ar  (VI)

in which Ar is as defined above and

Hal is iodine, bromine or chlorine in the presence of a catalyst.

In the context of the invention, all radical definitions, parameters and illustrations specified above and hereinbelow, in general or within areas of preference, i.e. the particular areas and areas of preference, may be combined as desired.

DETAILED DESCRIPTION OF THE INVENTION

Alkyl, Alkoxy, Alkylene and alkenylene are in each case independently a straight-chain, cyclic, branched or unbranched alkyl, alkoxy, alkylene or alkenylene radical respectively, each of which may optionally be further substituted by $C_1$-$C_4$-alkoxy. The same applies to the nonaromatic moiety of an arylalkyl radical.

$C_1$-$C_4$-Alkyl is, for example, methyl, ethyl, n-propyl, isopropyl, n-butyl, sec-butyl and tert-butyl, $C_1$-$C_8$-alkyl is additionally, for example, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, 1-ethyl-2-methylpropyl, n-heptyl and n-octyl, and $C_1$-$C_{12}$-alkyl is further additionally, for example, adamantyl, the isomeric menthyls, n-nonyl, n-decyl and n-dodecyl.

$C_1$-$C_4$-Alkoxy is, for example, methoxy, ethoxy, h-propoxy, isopropoxy, n-butoxy, sec-butoxy and tert-butoxy, $C_1$-$C_8$-alkoxy is additionally n-pentoxy, 1-methylbutoxy, 2-methylbutoxy, 3-methylbutoxy, neopentoxy, 1-ethylpropoxy, cyclohexoxy, cyclo-pentoxy, n-hexoxy and n-octoxy, and $C_1$-$C_{12}$-alkoxy is further additionally, for example, adamantoxy, the isomeric menthoxy radicals, n-decoxy and n-dodecoxy.

$C_1$-$C_8$-Alkylene is, for example, methylene, 1,1-ethylene, 1,2-ethylene, 1,1-propylene, 1,3-propylene, 1,4-butylene, 1,2-cyclohexoxylene and 1,2-cyclopentylene.

$C_2$-$C_8$-Alkenylene is, for example, 1,1-ethenylene, 2-ethoxy-1,1-ethenylene and 2-methoxy-1,1-ethenylene.

Fluoroalkyl and fluoroalkylene are in each case independently a straight-chain, cyclic, branched or unbranched alkyl radical and alkylene radical, respectively, each of which is singly, multiply or fully substituted by fluorine atoms and is in addition optionally singly or multiply substituted by chlorine atoms.

For example, $C_1$-$C_{12}$-fluoroalkyl is trifluoromethyl, chlorodifluoromethyl, 2,2,2-trifluoroethyl, pentafluoroethyl, nonafluorobutyl, heptafluoroisopropyl, perfluorooctyl, perfluorododecyl and perfluorohexadecyl.

Aryl is in each case independently a heteroaromatic radical having 5 to 14 framework carbon atoms of which no, one, two or three framework carbon atoms per cycle, but at least one framework carbon atom in the entire molecule, may be substituted by heteroatoms selected from the group of nitrogen, sulphur and oxygen, or preferably a carbocyclic aromatic radical having 6 to 14 framework carbon atoms.

Examples of mono-, bi- or tricyclic carbocyclic aromatic radicals having 6 to 14 framework carbon atoms are phenyl, biphenyl, naphthyl, phenanthrenyl, anthracenyl or fluorenyl and mono-, bi- or tricyclic heteroaromatic radicals having 5 to 14 framework carbon atoms of which no one, two or three framework carbon atoms per cycle, but at least one framework carbon atom in the entire molecule, may be substituted by heteroatoms selected from the group of nitrogen, sulphur and oxygen are, for example, pyridinyl, oxazolyl, benzofuranyl, dibenzofuranyl or quinolinyl.

In addition, the carbocyclic aromatic radical or heteroaromatic radical may be substituted by up to five identical or different substituents per cycle which are selected from the group of chlorine, fluorine, cyano, nitro, $C_1$-$C_{12}$-alkyl, $C_1$-$C_{12}$-fluoroalkyl, $C_1$-$C_{12}$-fluoroalkoxy, $C_1$-$C_{12}$-fluoroalkylthio, $C_1$-$C_{12}$-alkoxy, di($C_1$-$C_8$-alkyl)amino, tri($C_1$-$C_6$-alkyl)siloxyl or radicals of the formulae (IIIa) to (IIIf) as defined above.

Arylalkyl is in each case independently a straight-chain, cyclic, branched or unbranched alkyl radical as defined above which may be singly, multiply or fully substituted by aryl radicals as defined above.

The preferred substitution patterns are defined hereinbelow:

$R^1$ is preferably hydrogen, phenyl or $C_1$-$C_4$-alkyl, more preferably methyl.

$R^2$ is preferably $C_1$-$C_{12}$-fluoroalkyl, more preferably trifluoromethyl, chlorodifluoromethyl, 2,2,2-trifluoroethyl, pentafluoroethyl, nonafluorobutyl, heptafluoroisopropyl, perfluorooctyl, perfluorododecyl and perfluorohexadecyl, and even greater preference is given to trifluoromethyl.

$R^3$ is preferably hydrogen, $C_1$-$C_4$-alkyl, $C_5$-$C_{14}$-aryl or the following radicals which can be encompassed by the formulae (IIIa) to (IIIf):

—$CH_2CN$, —$CH_2COO(C_1$-$C_8$-alkyl), —$CH_2COO(C_5$-$C_{14}$-aryl), —$CH_2CONH(C_1$-$C_8$-alkyl), —$CH_2CON(C_1$-$C_8$-alkyl)$_2$, —$C(=CHOCH_3)COO(C_1$-$C_8$-alkyl), $C(=CHOCH_3)COO(C_5$-$C_{14}$-aryl), —$C(=CHOCH_3)CONH(C_1$-$C_8$-alkyl), and —$C(=CHOCH_3)CON(C_1$-$C_8$-alkyl)$_2$.

$R^3$ is more preferably $C_1$-$C_4$-alkyl or —$CH_2COO(C_1$-$C_8$-alkyl), and even greater preference is given to methyl.

Ar is preferably a phenyl or pyridyl radical which is non-, mono-, di- or trisubstituted by radicals which are selected from the group of nitro, cyano, chlorine, fluorine, $C_1$-$C_{12}$-alkyl, $C_1$-$C_{12}$-fluoroalkyl, $C_1$-$C_{12}$-fluoroalkoxy, $C_1$-$C_{12}$-fluoroalkylthio, $C_1$-$C_{12}$-alkoxy, di($C_1$-$C_8$-alkyl) amino, tri($C_1$-$C_6$-alkyl)siloxyl or radicals of the formulae (IIIa) to (IIIf) as defined above.

Ar is more preferably a phenyl radical which is non-, mono-, di- or trisubstituted by radicals which are selected from the group of chlorine, fluorine, $C_1$-$C_{12}$-alkyl, $C_1$-$C_{12}$-fluoroalkyl, $C_1$-$C_{12}$-fluoroalkoxy, $C_1$-$C_{12}$-fluoroalkylthio or $C_1$-$C_{12}$-alkoxy.

Ar is even more preferably a phenyl radical which is mono-, di- or trisubstituted by radicals which are selected from the group of fluorine, $C_1$-$C_4$-alkyl, $C_1$-$C_4$-fluoroalkyl, $C_1$-$C_4$-fluoroalkoxy or $C_1$-$C_4$-fluoroalkylthio, and greater preference is given to fluorine, trifluoromethyl, trifluoromethoxy and trifluoromethylthio, and even greater preference to trifluoromethyl.

Very particularly preferred Ar radicals include:
3,5-bis(trifluoromethyl)phenyl, 2,4-bis(trifluoromethyl)phenyl, 3,4-bis(trifluoromethyl)phenyl, 3-methyl-5-(trifluoromethyl)phenyl, 4-methyl-3-(trifluoromethyl)phenyl and 2-methyl-5-(trifluoro-methyl)phenyl.

A very particularly preferred compound of the formula (I) is 4-ethinyl-1,5-dimethyl-3-(trifluoromethyl)-1H-pyrazolyl-3,5-bis(trifluoromethyl)benzene.

In step a), compounds of the formula (IV) are converted to compounds of the formula (V) by halogenation and elimination.

The compounds of formula (IV) which are used as reactants are known from the literature or can be synthesized in a similar manner to the literature. For example, the parent pyrazoles can be acylated in a manner known per se.

In the process of the invention, the halogenation can be effected in a manner known per se, for example by reaction with phosphorus pentachloride, phosphorus pentabromide, mixtures of bromine and/or chlorine and triphenyl phosphite, and preference is given to the use of phosphorus pentachloride. Optionally, the reaction can be carried out in the presence of an organic solvent, although preference is given to the reaction without organic solvent.

Suitable organic solvents for the chlorination are, for example, aliphatic, alicyclic or aromatic, optionally halogenated hydrocarbons, for example benzine, benzene, toluene, xylene, chlorobenzene, dichlorobenzene, petroleum ether, hexane, cyclohexane, dichloromethane, chloroform or carbon tetrachloride.

The reaction temperature of the halogenation may, for example, be 0 to 150° C., and preferably 60 to 100° C., and the reaction pressure is, for example, 0.5 to 100 bar, preferably 0.9 to 5 bar, and even greater preference is given to ambient pressure.

The halogenation results in compounds of the formulae (IVa) and (IVb) which are likewise encompassed by the invention. In the formulae (IVa) and (IVb)

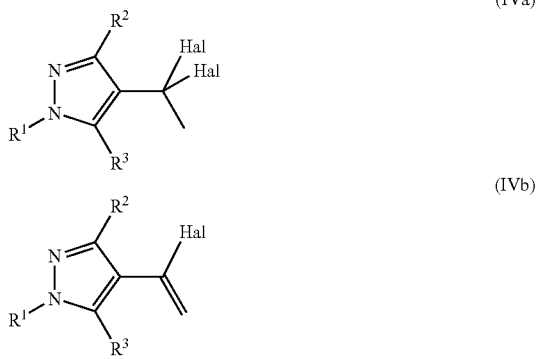

$R^1$, $R^2$ and $R^3$ are each as defined above including the areas of preference specified and Hal is in each case independently bromine, chlorine or fluorine, preferably bromine or chlorine and more preferably chlorine.

Preferred compounds of the formula (IVa) include:
4-(1,1-dichloroethyl)-1,5-dimethyl-3-(trifluoromethyl)-1H-pyrazole, 4-(1,1-dibromo-ethyl)-1,5 -dimethyl-3-(trifluoromethyl)-1H-pyrazole and 4-(1-bromo-1-chloroethyl)-1,5-dimethyl-3-(trifluoromethyl)-1H-pyrazole.

Preferred compounds of the formula (IVb) include:
4-(1-chloroethenyl)-1,5-dimethyl-3-(trifluoromethyl)-1H-pyrazole and 4(1-bromo-ethenyl)-1,5-dimethyl-3-(trifluoromethyl)-1H-pyrazole.

The elimination of step a) can then be carried out in an organic solvent in the presence of base.

The organic solvents used for the elimination are preferably polar, aprotic solvents. In this context, polar solvents are those which have a dielectric constant at 25° C. of 4 or more. Aprotic solvents are those which, based on an aqueous comparative scale, have a pKa value of 20 or more.

These include in particular ethers such as dioxane, tetrahydrofuran or ethylene glycol dimethyl or diethyl ether; sulphones such as tetramethylenesulphone and sulphoxides such as dimethyl sulphoxide, and preference is given to dimethyl sulphoxide.

The bases used may, for example, be alkali metal or alkaline earth metal hydrides, hydroxides, amides, alkoxides, for example sodium hydride, sodium amide, lithium diethylamide, sodium methoxide, sodium ethoxide, potassium tert-butoxide, sodium hydroxide, potassium hydroxide, tertiary amines such as trimethylamine, triethylamine, tributylamine, diisopropylethylamine, piperidine, N-methylpiperidine, N,N-dimethylaminopyridine, diazabicyclooctane (DABCO), diazabicyclononene (DBN) or diazabicycloundecene (DBU) or else N-heteroaromatic compounds, for example pyridine and 2-, 3- or 4-N,N-dimethylaminopyridine.

The elimination can be carried out, for example, at temperatures of −20 to 200° C., preferably at 20 to 180° C., more preferably at 80 to 180° C.

The reaction time may, for example, be 0.5 to 72 hours, and preferably 2 to 24 hours.

The pressure in the elimination is for example, 0.5 to 100 bar, and preferably 0.8 to 3 bar. Particular preference is given to ambient pressure.

In a preferred embodiment, the elimination may be effected without intermediate isolation and/or purification of the compounds of the formulae (IVa) and/or (IVb).

In step a), compounds of the formula (V) are obtained, which are likewise encompassed by the invention. The areas of preference specified above for $R^1$, $R^2$ and $R^3$ apply correspondingly.

A particularly preferred compound of the formula (V) is:
4-ethinyl-1,5-dimethyl-3-(trifluoromethyl)-1H-pyrazole In step b) of the process according to the invention, the compounds of the formula (V) are converted to compounds of the formula (I) by reacting with compounds of the formula (VI) in the presence of a catalyst.

Preferred catalysts are catalysts which contain palladium.

In a preferred embodiment, the process according to the invention is also carried out in the presence of base and/or copper salt, and particular preference is given to carrying out the process in the presence of base and copper salt.

The catalysts containing palladium which are used are, for example and with preference, palladium complexes. Palladium complexes can be generated, for example, in the reaction solution from palladium compounds and ligands, or in the form of already isolated palladium complexes, and preference is given to generating palladium complexes in the reaction solution.

Isolated palladium complexes which are suitable for the process according to the invention are, for example, palladium complexes which contain, as ligands, phosphorus compounds, for example phosphines, phosphites, phosphonites or mixtures thereof, preferably phosphines.

The palladium complexes which may contain phosphorus compounds as ligands are, for example and with preference, those of the formula (VIIa)

$$[PdL^1{}_2An_2] \qquad (VIIa)$$

in which $L^1$ is in each case a monophosphorus compound or $L^1{}_2$ together is a diphosphorus compound and An is an anion, preferably chloride, bromide, iodide, acetate, propionate, allyl or cyclopentadienyl, or those of the formula (VIIb)

$$[PdL^2{}_n] \qquad (VIIb)$$

in which n is 2, 3 or 4 and in which $L^2$ may in each case be a monophosphorus compound or half an equivalent of a diphosphorus compound.

Monophosphorus compounds are, for example and with preference, those of the formula (VIIIa)

$$P(G-R^7)_3 \qquad (VIIIa)$$

in which

G is in each case independently, and independently of $R^7$, absent or is oxygen, and the $R^7$ radicals are in each case independently $C_1$-$C_8$-alkyl or unsubstituted, mono-, di- or tri-$R^8$-substituted phenyl, naphthyl or ferrocenyl, where R⁸ is $C_1$-$C_8$-alkyl, $C_1$-$C_8$-alkoxy, chlorine, fluorine, N($C_1$-$C_6$-alkyl)$_2$, $CO_2$—($C_1$-$C_6$-alkyl), —CON($C_1$-$C_6$-alkyl)$_2$, cyano or CO($C_1$-$C_6$-alkyl).

Particularly preferred monophosphorus compounds are those of the formula (VIIIa) in which G is absent and R⁷ is in each case independently $C_1$-$C_8$-alkyl or unsubstituted, mono-, di- or tri-R⁸-substituted phenyl or naphthyl or ferrocenyl, where R⁸ is $C_1$-$C_8$-alkyl, $C_1$-$C_8$-alkoxy, chlorine or fluorine.

Even greater preference is given to the monophosphorus compounds being triphenylphosphine, phenyldi(tert-butyl) phosphine and tri(tert-butyl)phosphine.

Diphosphorus compounds may be, for example and with preference, those of the formula (VIIIb)

(R⁹-G)$_2$P-G-Z-G-P(G-R⁹)$_2$         (VIIIb)

in which

G is in each case independently, and independently of R⁹ and Z, absent or is oxygen and the R⁹ radicals are each independently $C_1$-$C_8$-alkyl or unsubstituted, mono-, di- or tri-R¹⁰-substituted phenyl, naphthyl or heteroaryl having 5 to 12 framework carbon atoms, where R¹⁰ is in each case independently selected from the group of $C_1$-$C_8$-alkyl, $C_1$-$C_8$-alkoxy, fluoro- and cyano, and Z is an unsubstituted or substituted radical from the group of $C_1$-$C_4$-alkylene, 1,2-phenylene, 1,3-phenylene, 1,2-cyclohexyl, 1,1'-ferrocenyl, 1,2-ferrocenyl, 2,2'-(1,1'-binaphthyl) and 1,1'-biphenyl.

Preferred diphosphorus compounds are 1,3-bis(diisopropylphosphino)propane, 1,4-bis(diisopropylphosphino)butane, 2,2'-bis(diphenylphosphino)-1,1'-binaphthyl.

Preference is given to using complexes which contain monophosphorus compounds as ligands.

Preferably isolated palladium complexes are bis(triphenylphosphine)palladium(II) dichloride, bis(tricyclohexylphosphine)palladium(II) dichloride, bis(di-tert-butylphenylphosphine)palladium(II) dichloride, bis(tri-tert-butylphosphine)palladium(II) dichloride, tricyclohexylphosphinepalladium(0) diallyl ether complex, bis(tricyclohexylphosphine)palladium(0) and tetrakis(triphenylphosphine)palladium(0).

Preferred palladium catalysts for the process according to the invention are palladium complexes which are generated in the reaction solution from palladium compounds and ligands.

The palladium compounds used may be, for example and with preference: dibenzylideneacetone palladium(0) complexes or allylpalladium chloride or bromide or those of the formula Pd(Y¹)$_2$         (IXa)

in which

Y¹ is an anion, preferably chloride, bromide, acetate, propionate, nitrate, methanesulphonate, trifluoromethanesulphonate, acetylacetonate, allyl or cyclopentadienyl, or palladium compounds of the formula (IXb)

Pd(Y²)$_2$L³$_2$         (IXb)

in which

Y² is an anion, preferably chloride, bromide, acetate, methanesulphonate, nonafluorobutanesulphonate, trifluoromethanesulphonate, tetrafluoroborate or hexafluorophosphate and L³ is in each case a nitrile, preferably acetonitrile, benzonitrile or benzyl nitrile, or an olefin, preferably cyclohexene or cyclooctene, or L³$_2$ together is a diolefin, preferably norbornadiene or 1,5-cyclooctadiene, or palladium compounds of the formula (IXc)

M$_2$[Pd(Y³)$_4$]         (IXc), where

Y³ is a halide, preferably chloride or bromide and

M is lithium, sodium, potassium, ammonium or organic ammonium.

Preferred palladium compounds are palladium(II) acetate, palladium(II) chloride, palladium(II) bromide, palladium(II) propionate, palladium(II) acetylacetonate, lithium, sodium or potassium tetrachloropalladate, bis(benzonitrile)palladium(II) chloride, bis(acetonitrile)palladium(II) chloride.

For the generation of palladium complexes in the reaction solution, ligands used are preferably phosphorus compounds of the formulae (VIIIa) and (VIIIb), and even greater preference is given to monophosphorus compounds of the formula (VIIIa). The areas of preference specified apply in the same manner.

The molar ratio of phosphorus to palladium in the reaction mixture may be, for example, 1:1 to 10:1, preferably 2:1 to 5:1, and more preferably 3:1 to 4:1.

The molar ratio of compounds of the formula (VI) to palladium may be, for example, 10 to 20000, preferably a ratio of 100 to 5000, and most preferably 500 to 2000.

Step b) of the process according to the invention is preferably carried out in the presence of at least one, preferably one, base.

Suitable bases are, for example, amines of the formula (X)

NH$_m$(R¹¹)$_{(3-m)}$         (X)

in which m is zero, one or two and the R¹¹ radicals are each independently $C_1$-$C_{12}$-alkyl, $C_5$-$C_{14}$-aryl or $C_6$-$C_{15}$-arylalkyl, or in each case two or three of the R¹¹ radicals together with the nitrogen atom may form a mono-, bi- or tricyclic heterocycle having 4 to 8 carbon atoms per cycle.

Also suitable as bases are N-heteroaromatic compounds. These are, for example, optionally substituted pyridines, in particular pyridine, 2,6-bis(diisopropyl)pyridine and dimethylaminopyridine.

Also suitable as bases are, for example, alkali metal and/or alkaline earth metal salts of aliphatic or aromatic carboxylic acids such as acetates, propionates and benzoates, and/or carbonates, for example sodium carbonate and potassium carbonate, hydrogencarbonates, for example sodium hydrogencarbonate and potassium hydrogencarbonate, phosphates, hydrogenphosphates and/or hydroxides, for example sodium hydroxide or potassium hydroxide.

Very particularly preferred bases for step b) of the process according to the invention are diethylamine, triethylamine, ethyldiisopropylamine, di-n-propylamine, tri-n-propylamine, diisopropylamine, triisopropylamine, diisobutylamine, triiso-butylamine, dicyclohexylamine, dicyclohexylmethylamine, cyclohexyldimethylamine and 2,6-bis(diisopropyl)pyridine, and even greater preference is given to diethylamine and triethylamine.

The molar amount of the base used may be, for example, 0.8 to 200 times, preferably 1 to 3 times and more preferably 1.0 to 1.2 times, the molar amount of the compound of the formula (VI). Bases which are liquid under the reaction conditions can also be used as a solvent.

For step b), preference is also given to using copper salts, in particular copper(I) and copper(II) salts.

The anions of these salts may be halides, pseudohalides, carboxylates, perfluoroalkylsulphonates, sulphates, nitrates, carbonates, hydroxides.

Preferred halides and pseudohalides are fluoride, chloride, bromide, iodide, cyanide, cyanate, thiocyanate, preferred carboxylates are acetate and propionate, and preferred perfluoroalkylsulphonates are triflate and nonaflate.

Preference is also given to thioether, phosphite and phosphine adducts to copper(I) salts.

Particularly preferred copper salts are copper(I) iodide, copper(I) bromide, copper(I) chloride and copper(I) bromide-dimethyl sulphide complex.

The copper salt can be used, for example, in amounts of 0.01 to 100 mol %, based on the compounds of the formula (VI), preferably in amounts of 0.1 to 20 mol % and more preferably in amounts of 0.5-5 mol %. It is also possible to use combinations of a plurality of salts.

Step b) of the process according to the invention is optionally carried out in the presence of organic solvent, preferably in the presence of aprotic solvent, more preferably in the presence of polar aprotic solvents. The above definitions of aprotic and polar apply correspondingly.

Particularly suitable solvents for step b) are ethers, for example dioxane, THF, 1,2-dimethoxyethane, diethylene glycol dimethyl ether, tetraethylene glycol dimethyl ether, amidic solvents, for example dimethylformamide, N-methylpyrrolidone, N-methylcaprolactam or dimethylacetamide, sulphoxides and sulphones, for example dimethyl sulphoxide or tetramethylenesulphone, nitriles, for example acetonitrile, benzonitrile and benzyl nitrile, and ketones, for example dimethyl ketone, diethyl ketone, methyl tert-butyl ketone. Bases which are liquid under the reaction conditions, in particular amines, can also optionally be added as a solvent.

The reaction temperature in step b) may be, for example, 0° C. to 200° C., preferably 50 to 150° C. and more preferably 50° C. to 100° C., and the reaction pressure may be, for example, 0.2 to 100 bar. Preference is given to ambient pressure.

Step b) is carried out preferably but not obligatorily under a protective gas atmosphere with substantial exclusion of oxygen and moisture. Useful protective gases are, for example, nitrogen and noble gases, for example argon, or mixtures of such gases.

In a preferred embodiment of the process according to the invention, a reaction vessel is additionally charged with the compounds of the formula (V), the compounds of the formula (VI), base, copper salt, ligand and palladium compound under protective gas and the mixture is heated with stirring to the reaction temperature. On completion of reaction, the mixture is poured onto water. Solid products then precipitate out and can be filtered off with suction and washed, for example, with water. Liquid products can be extracted with an organic, water-miscible or sparingly water-miscible solvent, and worked up, for example distillatively.

Solid products may optionally be further purified, for example, by recrystallization or reprecipitation.

It would be advantageous to carry out the reaction with controlled metering. Controlled metering means that at least one component selected from compound of the formula (VI), compound of the formula (V) and palladium compound is metered in in the course of the reaction.

It would also be advantageous to add free-radical inhibitors, for example 2,6-di-tert-butylphenol, to the reaction mixture in step b), in order to substantially prevent undesired side reactions.

In the inventive manner, the compounds of the formula (I) are obtained in good yields.

The compounds of the formula (I) which can be prepared in accordance with the invention, and also the compounds of the formulae (IVa), (IVb) and (V) are suitable in particular for use in a process for preparing agrochemicals. Preferred agrochemicals are those which are used as insecticides and acaricides. These are in particular those which are specified in EP-A 571 326 and EP-A 1 219 173.

The advantage of the process according to the invention lies in its ease of performability and the good yields of pyrazolylalkines.

EXAMPLES

Example 1

Preparation of 1,5-dimethyl-3-trifluoromethyl-1H-pyrazole 187 ml (1.32 mol) of trifluoroacetic anhydride are added dropwise to a solution of 95.4 g (1.32 mol) of isopropenyl methyl ether in 265 ml of tert-butyl methyl ether and 107 ml (1.32 mol) of pyridine at a temperature of 0° C. to +5° C. After a reaction time of 30 min at +5° C., the reaction mixture is washed with 400 ml of water and 200 ml of a saturated $Na_2CO_3$ solution. The organic phase is removed and dried over $MgSO_4$. The solution is cooled to a temperature of −20° C. and 70.4 ml (1.32 mol) of methylhydrazine are added dropwise thereto. The reaction mixture is allowed to gradually come to room temperature, the organic phase is dried over $MgSO_4$, and the solution is subsequently concentrated under reduced pressure. Distillation of the oily residue results in 186 g (1.13 mol; 83%) of 1,5-dimethyl-3-trifluoromethyl-1H-pyrazole (b.p.: 71° C. /12 mbar).

Example 2

Preparation of 4-acetyl-1,5-dimethyl-3-trifluoromethyl-1H-pyrazole 22.6 g (0.138 mol) of 1,5-dimethyl-3-trifluoromethyl-1H-pyrazole are added dropwise at 0° C. to a solution of 156 ml (1.65 mol) of acetic anhydride and 0.5 ml of conc. $H_2SO_4$. The reaction mixture is stirred under reflux for approx. 8 days. After each 24 h of reaction time, 0.5 ml of $H_2SO_4$ each time is added to the reaction mixture. On completion of the reaction, excess acetic anhydride is distilled off under reduced pressure, the residue is taken up in 500 ml of $CH_2Cl_2$ and the organic phase is washed 3 times with 300 ml of water each time. The organic phase is dried over $MgSO_4$ and concentrated by rotary evaporation. Distillation of the oily residue results in 6.20 g (0.030 mol; 21.8%) of 4-acetyl-1,5-dimethyl-3-trifluoromethyl-1H-pyrazole (b.p.: 142° C./0.4 mbar).

Example 3

Preparation of 4-ethinyl-1,5-dimethyl-3-(trifluoromethyl)-1H-pyrazole

A mixture of 12.3 g (0.056 mol) of 4-acetyl-1,5-dimethyl-3-trifluoromethyl-1H-pyrazole and 14.1 g (0.068 mol) of $PCl_5$ is heated to 85° C. and stirred at this temperature for 18 h. After the end of the reaction, the $POCl_3$ formed is distilled off under reduced pressure, and the residue is taken up in 70 ml of dimethyl sulphoxide and admixed at room temperature with 6.94 g (0.124 mol) of KOH in 13.2 ml of water. The reaction mixture is heated to reflux with stirring for 18 h. On completion of the reaction, the mixture is added to 200 ml of ice-water and extracted 3 times with 100 ml of tert-butyl methyl ether. The combined organic phases are dried over $Na_2SO_4$. Removal of the solvents under reduced pressure and recrystallization from EtOH result in 5.4 g (0.029 mol; 52%) of 4-ethinyl-1,5-dimethyl-3-(trifluoromethyl)-1H-pyrazole as a yellow solid.

Example 4

Preparation of 4-ethinyl-1,5-dimethyl-3-(trifuoromethyl)-1H-pyrazolyl-3,5-bis(trifluoromethyl)benzene 183 mg (0.983 mmol) of 4-ethinyl-1,5-dimethyl-3-(trifluoromethyl)-1H-pyrazole, 2.3 mg (0.01 mmol) of palladium acetate, 10.7 mg (0.04 mmol) of triphenylphosphine and 3.9 mg (0.02 mmol) of copper(I) iodide are weighed into a round-bottom flask and placed under protective gas. Subsequently, 300 mg (1.03 mmol) of 3,5-bis(trifluoromethyl)bromobenzene and diethylamine (5 ml) are added and the mixture is heated to reflux temperature for 12 h. After the end of the reaction, the mixture is cooled, poured onto cold, dilute hydrochloric acid and extracted with ether. The combined ether phases which have been dried over $MgSO_4$ are concentrated. The product is obtained as a slightly brownish solid in a 91% yield.

Example 5

Preparation of 4-ethinyl-1,5-dimethyl-3-(trifluoromethyl)-1H-pyrazolyl-3,5-bis(trifluoromethyl)benzene 183 mg (0.983 mmol) of 4-ethinyl-1,5-dimethyl-3-(trifluoromethyl)-1H-pyrazole, 2.3 mg (0.01 mmol) of palladium acetate and 3.9 mg (0.02 mmol) of copper(I) iodide are weighed into a round-bottom flask and placed under protective gas. Subsequently, 9.1 mg (0.04 mmol) of di(tertbutyl)phenylphosphine, 300 mg (1.03 mmol) of 3,5-bis(trifluoromethyl)bromobenzene, 137 mg (1.08 mmol) of cyclohexyldimethylamine and dimethylacetamide (5 ml) are added and the mixture is heated to 110° C. for 12 h. After the end of the reaction, the mixture is cooled, poured onto cold, dilute hydrochloric acid and extracted with ether. The combined ether phases which have been dried over $MgSO_4$ are concentrated. The product is obtained as a solid in an 85% yield.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:
1. Process for preparing compounds of the formula (I)

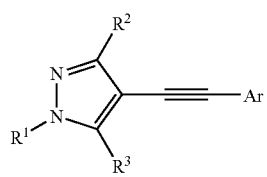

(I)

in which $R^1$ is hydrogen, $C_1$-$C_{12}$-alkyl, $C_5$-$C_{14}$-aryl, $C_6$-$C_{15}$-arylalkyl, $C_1$-$C_{12}$-fluoroalkyl or radicals of the formula (II)

($C_1$-$C_8$-alkylene)-B-D-E     (II)

and $R^2$ and $R^3$ are each independently hydrogen, $C_1$-$C_{12}$-alkyl, $C_1$-$C_{12}$-alkoxy, $C_5$-$C_{14}$-aryl, $C_5$-$C_{14}$-aryloxy, $C_6$-$C_{15}$-arylalkyl, $C_6$-$C_{15}$-arylalkoxy, chlorine, fluorine, cyano, free or protected formyl, $C_1$-$C_{12}$-fluoroalkyl, $C_1$-$C_{12}$-fluoroalkylthio, $C_1$-$C_{12}$-fluoroalkoxy or radicals of the formulae (IIIa) to (IIIf)

| A-B-D-E | (IIIa) |
|---|---|
| A-E | (IIIb) |
| A-$SO_2$-E | (IIIc) |
| A-B-$SO_2R^5$ | (IIId) |
| A-$SO_3$W | (IIIe) |
| A-COW | (IIIf) | where, in the formulae (II) and (IIIa) to (IIIf),

A is absent or is a $C_1$-$C_8$-alkylene, $C_1$-$C_8$-alkenylene or $C_1$-$C_8$-fluoroalkylene radical and B is absent or is oxygen, sulphur or $NR^4$ where $R^4$ is hydrogen, $C_1$-$C_8$-alkyl, $C_6$-$C_{15}$-arylalkyl or $C_5$-$C_{14}$-aryl and D is a carbonyl group and E is $R^5$, $OR^5$, $NHR^6$ or $N(R^6)_2$, where $R^5$ is $C_1$-$C_8$-alkyl, $C_6$-$C_{15}$-arylalkyl or $C_5$-$C_{14}$-aryl and $R^6$ is in each case independently $C_1$-$C_8$-alkyl, $C_6$-$C_{15}$-arylalkyl or $C_6$-$C_{14}$-aryl, or $N(R^6)_2$ together is a cyclic amino radical having 4 to 12 carbon atoms and W is OH, $NH_2$ or OM where M is an alkali metal ion, half an equivalent of an alkaline earth metal ion, an ammonium ion or an organic ammonium ion and Ar is a mono-, bi- or tricyclic aromatic radical having a total of 5 to 18 ring atoms, and in which at most one ring atom per cycle is selected from the group of oxygen, sulphur and nitrogen, and the mono-, bi- or tricyclic aromatic radical is optionally mono- or polysubstituted, comprising in one step, a), converting the compounds of the formula (IV)

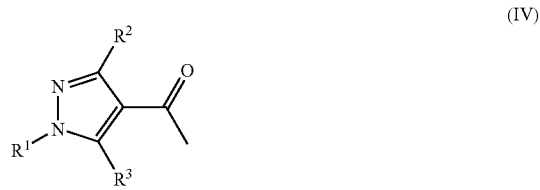

(IV)

in which $R^1$, $R^2$ and $R^3$ are each independently as defined above, by halogenation and elimination to compounds of the formula (V)

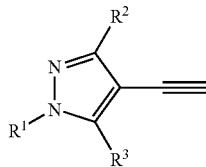

(V)

in which $R^1$, $R^2$ and $R^3$ are each independently as defined above
and
in one step, b), converting the compounds of the formula (V) to compounds of the formula (I) by reacting with compounds of the formula (VI)

Hal-Ar  (VI)

in which Ar is as defined above and
Hal is iodine, bromine or chloroine,
in the presence of a catalyst.

2. Process according to claim 1, characterized in that $R^1$ is hydrogen, phenyl or $C_1$-$C_4$-alkyl.

3. Process according to claim 1, characterized in that $R^2$ is $C_1$-$C_{12}$-fluoroalkyl.

4. Process according to claim 1, characterized in that $R^3$ is hydrogen, $C_1$-$C_4$-alkyl, $C_5$-$C_{14}$-aryl or the radicals selected from the group consisting of:
—$CH_2CN$, —$CH_2COO(C_1$-$C_8$-alkyl), —$CH_2COO(C_5$-$C_{14}$-aryl), —$CH_2CONH(C_1$-$C_8$alkyl), —$CH_2CON(C_1$-$C_8$-alkyl)$_2$, —$C(=CHOCH_3)COO(C_1$-$C_8$-alkyl)$, $C(=CHOCH_3)COO(C_5$-$C_{14}$-aryl), —$C(=CHOCH_3)CONH(C_1$-$C_8$-alkyl), and —$C(=CHOCH_3)CON(C_1$-$C_8$-alkyl)$_2$.

5. Process according to claim 1, characterized in that Ar is a phenyl or pyridyl radical which is non-, mono-, di- or trisubstituted by radicals which are selected from the group of chlorine, fluorine, $C_1$-$C_{12}$-alkyl, $C_1$-$C_{12}$-fluoroalkyl, $C_1$-$C_{12}$-fluoroalkoxy, $C_1$-$C_{12}$-fluoroalkylthio, $C_1$-$C_{12}$-alkoxy, di($C_1$-$C_8$-alkyl)amino, tri($C_1$-$C_6$-alkyl)siloxyl or radicals of the formulae (IIIa) to (IIIf) as defined in claim 1.

6. Process according to claim 1, characterized in that Ar is a phenyl radical which is non-, mono-, di- or trisubstituted by radicals which are selected from the group of chlorine, fluorine, $C_1$-$C_{12}$-alkyl, $C_1$-$C_{12}$-fluoroalkyl, $C_1$-$C_{12}$-fluoroalkoxy, $C_1$-$C_{12}$-fluoroalkylthio or $C_1$-$C_{12}$-alkoxy.

7. Process according to claim 1, characterized in that 4-ethinyl-1,5-dimethyl-3-(trifluoromethyl)-1H-pyrazolyl-3,5-bistrifluoromethyl)benzene is prepared.

8. Process according to claim 1, characterized in that the halogenation is effected by reacting with phosphorus pentachloroide, phosphorus pentabromide, mixtures of bromine and/or chlorine or triphenyl phosphite.

9. Process according to claim 1, characterized in that the elimination of step a) is carried out in an organic solvent in the presence of base.

10. Process according to claim 1, characterized in that the catalysts used contain palladium.

11. Process according to claim 1, characterized in that step b) is carried out in the presence of base and/or copper salt.

12. Process according to claim 10, characterized in that the catalyst used contains palladium which is a palladium complex.

13. Process according to claim 12, characterized in that the palladium complexes are generated in the reaction solution from palladium compounds and ligands.

14. Process according to claim 10, characterized in that the molar ratio of compounds of the formula (VI) to palladium is 10 to 20 000.

15. Process according to claim 11, characterized in that the bases used are:
amines of the formula (X)

$NH_m(R^{11})_{(3-m)}$  (X)

in which
m is zero, one or two and
the $R^{11}$ radicals are each independently $C_1$-$C_{12}$-alkyl, $C_5$-$C_{14}$-aryl or $C_6$-$C_{15}$-arylalkyl, or two or three of the $R^{11}$ radicals together with the nitrogen atom optionally form a mono-, bi- or tricyclic heterocycle having 4 to 8 carbon atoms per cycle and/or
N-heteroaromatic compounds or
alkali metal and/or alkaline earth metal salts of aliphatic or aromatic carboxylic acids and/or carbonates, hydrogencarbonates, phosphates, hydrogenphosphates and/or hydroxides.

16. Process according to claim 11, characterized in that copper (I) and copper(II) salts of halides, pseudohalides, carboxylates, perfluoroalkylsulphonates, sulphates, nitrates, carbonates and hydroxides, and/or thioether, phosphite and phosphine adducts of copper(I) salts are used.

17. Process according to claim 11, characterized in that it is carried out with controlled metering.

18. A process for preparing agrochemicals comprising incorporating compounds which have been prepared according to claim 1.

* * * * *